United States Patent [19]

Kino et al.

[11] Patent Number: 4,724,146

[45] Date of Patent: * Feb. 9, 1988

[54] METHOD FOR PREPARATION HERPES SIMPLEX VIRUS SUBUNIT VACCINE

[75] Inventors: Youichiro Kino; Hiroshi Mizokami, both of Kumamoto; Tetsuo Kawahara, Ohzu, all of Japan

[73] Assignee: Juridical Foundation The Chemo-Sero-Therapeutic Research Institute, Kumamoto, Japan

[ * ] Notice: The portion of the term of this patent subsequent to May 7, 2002 has been disclaimed.

[21] Appl. No.: 768,720

[22] Filed: Aug. 23, 1985

[30] Foreign Application Priority Data

Aug. 24, 1984 [JP] Japan .................. 59-177194

[51] Int. Cl.[4] .................. A61K 39/12; C12N 7/02; C12N 7/00
[52] U.S. Cl. .................. 424/89; 435/235; 435/239; 530/412; 530/826
[58] Field of Search .................. 424/89; 435/235, 238, 435/239; 530/412, 413, 417, 826

[56] References Cited

U.S. PATENT DOCUMENTS

| | | | |
|---|---|---|---|
| 3,920,625 | 11/1975 | Andersson et al. | 530/382 |
| 4,138,287 | 2/1979 | Andersson et al. | 424/89 X |
| 4,317,811 | 3/1982 | Bertland et al. | 424/89 |
| 4,452,734 | 6/1984 | Larson et al. | 260/112 R |
| 4,515,714 | 5/1985 | Kawahara et al. | 424/89 X |

FOREIGN PATENT DOCUMENTS 0001365  4/1979  European Pat. Off. .
0048201  3/1982  European Pat. Off. .
83/02897  9/1983  PCT Int'l Appl. .................. 424/89

OTHER PUBLICATIONS

Zweerink et al., Infect. Immun., 31, 267–275, (1981).
Kutinova et al., Arch. Virol., 61, 141–147, 1979.
Nahmias et al., *The Human Herpes Viruses,* pp. 503–509, Elsevier, N.Y., 1981.
Klein et al., Arch. Virol., 68, 73–80, (1981).
Kitces et al., Infect. Immun., 16, 955–960, (1977).
Skinner et al., Med. Microb. Immunol., 166, 119–132, (1978).
Cappel et al., Arch. Virol., 65, 15–23, (1980).
Eberle et al., J. Virol., 36, 665–675, (1980).
Chemi. Ab., vol. 92, p. 439, No. 92514w, (1980).
Biol. Ab., vol. 79, (2) No. 13305, (1985).
Chemi. Ab., vol. 102, p. 430, No. 147161m, (1985).

*Primary Examiner*—Esther M. Kepplinger
*Assistant Examiner*—Shawn P. Foley
*Attorney, Agent, or Firm*—Fleit, Jacobson, Cohn & Price

[57] ABSTRACT

A method for the preparation of an herpes simplex virus subunit vaccine, which comprises subjecting a solution containing glycoproteins gA and gB to column chromatography using, as a gel for chromatography, sulfuric acid ester of cellulose or a crosslinked polysaccharide to adsorb the glycoproteins gA and gB onto the gel in the presence of an anionic surfactant or a nonanionic surfactant, eluting the adsorbed glycoproteins to obtain an eluate containing the glycoproteins, and subjecting the eluate to gel filtration to obtain a filtrate containing the glycoproteins.

4 Claims, No Drawings

METHOD FOR PREPARATION HERPES SIMPLEX VIRUS SUBUNIT VACCINE

The present invention relates to a method for the preparation of a herpes simplex virus subunit vaccine. More particularly, it relates to a herpes simplex virus subunit vaccine which comprises, as an effective component glycoproteins gA and gB, which are present in both herpes simplex virus type 1 and type 2, said subunit vaccine being useful for prophilaxis of infection by herpes simplex virus type 1 and type 2.

TECHNICAL BACKGROUND AND FIELD OF THE INVENTION

Infection diseases induced by various viruses are almost controlled by vaccination, but the prevention of infection due to herpes simplex virus is still a serious problem. In case of first infection in adult, the symptoms are usually very severe, and in developed countries, the population having antibodies against herpes simplex virus (hereinafter, referred to as "HSV") is decreasing. This problem will become more important in future. In some countries, it is considered as a kind of venereal disease or a neonatal herpes infection.

There are two types of virus in HSV, i.e. type 1 and type 2, and the type 1 virus infects mainly around lip, and the type 2 virus infects mainly around genitals.

It is known that both types of viruses are fairly distributed in Japan, and hence, it is important to take effective measures for prophylaxis of the virus infection in future.

Most effective prophylactic measures against virus infections are administration of a vaccine. However, in the case of HSV, development of vaccine is inhibited because of the specific properties of HSV, i.e. carcinogenicity and latent infection of the virus. It is very difficult to confirm that the infectiousness of HSV is removed in a live vaccine prepared from an attenuated virus or in an inactivated vaccine prepared by inactivating the virus by conventional inactivation processes, such as addition of inactivating agents or heat-treatment. If a viral infectiousness is remained in the vaccine, it may induce serious symptom to human body. When such a vaccine is innoculated to human, even though a symptom does not appear immediately, there is a possibility of latent infection. Thus, it is very difficult to prove the safety in HSV vaccine. In other aspect, the vaccine to be used for protection to the infection having low lethal rate such as herpes simplex infection must highly be purified in order to eliminate undesirable side effect. From these viewpoints, the conventional live vaccine and inactivated vaccine are not practically useful.

PRIOR ART

Under the circumstances, various studies have been done in order to develop a new vaccine having no danger of HSV infection due to vaccination, among which there are some reports on HSV subunit vaccine which might have a possibility of practical use.

It is known that specific glycoproteins of HSV are present in virus envelope which is surface region of HSV particles and also in the cell membrane of infected culture cells, and it has been considered that an antibody for preventing HSV infection. Based on the assumption, it has been tried to use, for example, virus envelope components as a vaccine stock.

Skinner et al. have tried to use as a vaccine stock a part of fractions obtained form kidney cells of brephic hamster (BHK-21) infected with HSV type 1, which are prepared by destroying the kidney cells by ultrasonic treatment, dissolving the cells by adding thereto 1 v/v % of Nonidet P-40 (NP-40, manufactured by Shell Chemical), inactivating the virus by treating with formalin at 4° C. for 72 hours, and then subjecting the mixture to a cushion ultracentrifugation using 20 w/v % sucrose solution [cf. Med. Microbiol. Immunol., 166, 119–132 (1978)].

Kutinova et al. have tried to use as a vaccine stock a supernatant obtained from human embryonic lung cells infected with HSV type 1, which is prepared by adding 0.5 v/v % Nonidet P-40 to a suspension of the cells and thereby dissolving the cells, and removing nucleus substances of the cells and nucleocapsid of virus form the dissolved cells by centrifugation [cf. Arch. Virol., 61, 141–147 (1979)].

Zweerink et al. have reported to use as a vaccine stock a component of a primary kidney cells of rabbit infected with HSV type 1, which is prepared by dissolving the kidney cells infected with HSV type 1 with Tris-EDTA buffer containing 1 v/v % Triton X-100, removing the nucleus substances of the cells by low speed centrifugation, removing high molecular weight substances by high speed centrifugation, passing the resulting supernatant through an affinity column packed with Sepharose 4B bound with lentil lectin, and eluting the adsorbed components with an eluting solution containing α-methylmannoside and glucose [cf. Infect. Immun., 31, 267–275 (1981)].

Bertland et al. have used as a vaccine stock a virus envelope form chicken embryo fibroblast infected with HSV type 1, which is prepared by dissolving the chicken embryo fibroblast with a phosphate buffer containing 4 mole of urea, separating the cell components by continuous ultracentrifugation, inactivating the virus components contained in the supernatant by subjecting it to ultrasonic treatment and heat treatment at 60° C. for 3 hours, decomposing the virus DNA with deoxyribonuclease, by which the virus envelope components is isolated [cf. U.S. Pat. No. 4,317,811 (1982)].

Another aspect has been done by Klein et al. [cf. Arch. Virol., 68, 73–80 (1981)], that is, a culture supernatant of Vero cells infected with HSV type 1 is subjected to continuous ultracentrifugation with sucrose density gradient to obtain purified virus particles, and a suspension of the virus particles is treated with 1 v/v % Triton X-100 to destroy the virus particles, and then the resultant is subjected to ultracentrifugation with sucrose density gradient to separate into HSV nucleocapsid and virus envelope component, and the latter component is used as a vaccine stock.

Kitces et al. have used as a vaccine stock a virus envelope component having no HSV-originated nucleic acid obtained form human pharyngeal cancer epithelial cells (Hep-2 cells) infected with HSV type 1, which is prepared by destroying the epithelial cells with homogenizer, centrifuging the homogenized mixture to separate a supernatant of virus particle suspension, subjecting the supernatant to inactivation with formalin, adding 1 w/v % of sodium dodecylsulfate and N-lauroylsurcosine sodium salt to the virus particle suspension in order to dissolve them, subjecting the mixture to ultracentrifugation with cesium chloride to collect a nucleocapsid-free supernatant, treating it with deoxyribonuclease to give the desired virus envelope having no nucleic acid [cf. Infect. Immun., 16, 955–960 (1977)].

Cappel et al. have tried to use as a vaccine stock a virus envelope component from chicken embryo fibroblast infected with HSV type 1, which is prepared by subjecting repeatedly the cells to ultrasonic treatment and freezing-thawing in order to destroy the cells, subjecting the resulting mixture to a low centrifugation and ultrafiltration to partially purify the virus particles, subjecting the crude virus particles to sugar density gradient ultracentrifugation twice to give purified virus particles, dissolving the particles with 1 v/v % Nonidet P-40, and subjecting the solution to sugar solution cusion ultracentrifugation to collect the desired virus envelope component.

The above reports are all concerned with HSV type 1, and as to HSV type 2, it is also reported by Hilleman et al. that a subunit vaccine is obtained by subjecting chicken embryo fibroblast infected with HSV type 2 to dissolving treatment with Triton X-100, treating the mixture with deoxyribonuclease, subjecting the mixture to lectin affinity chromatography and Sepharose gel filtration to collect virus glycoproteins and then treating it with aluminum gel a[cf. The Human Herpes Viruses, 503–509, by Nahmias, A. J. et al., Elsevier, N.Y. (1981)].

In these reports, partially purified virus envelope is used as the virus stock and is treated with aluminum hydroxide gel in order to incease immunogenicity. It has experimentally been confirmed in mice that the virus envelope is effective as a virus stock, but the process for the preparation thereof is very complicated in the purification step, and further, the purification is not sufficient and hence it is contaminated with culture cell components.

It is very important, as mentioned above, that a vaccine for HSV must be highly purified in order to avoid undesirable side effect as low as possible. It is assumed that the known vaccines are contaminated with a fairly amount of proteins from the host, even through the vaccine stock is obtained by extracting it from infected cells or virus particles. Thus, the known vaccines are hardly acceptable as an HSV subunit vaccine for human in view of less safety.

It is reported by Eberle et al. that anti-sera, which has neutralizing activity against purified HSV-1 particle against gA and gB are prepared by dissolving treatment human pharyngeal cancer epithelial cells infected with HSV with 1 % deocycholic acid and 1 % Tween 40, several times subjecting the mixture to prepartive sodium dodecyl sulfate polyacrylamide gel electrophresis and sodium dodecyl sulfate-hydroxyapatite column chromatography to purify subunit gA and gB.

Eberle et al. also suggested that gA and gB are not the same but they have quite similar antigenic determinant sites, and that their binding rate with glucide are different while their component protein are the same since anti-gA sera and anti-gB sera react with gB and gA respectively. However, because gA and gB share antigenic determinants and gA can be changed into gB, it has now been agreed that the glycoprotein gA be designated pgB, a precursor to gB at the International Herpes Virus Workshop in Oxford England (1983).

The vaccine stock used for a subunit vaccine against HSV should most preferably have antigenic determinants common to HSV type 1 and type 2 and the antigenicity is not sufficient by mere producibility of neutralizing antibody against the virus but should be capable of completely prohibiting the HSV infection. Moreover, as is mentioned above, the vaccine product should have high safety and excellent effectiveness and also sufficient storage stability in the form of a vaccine preparation. Thus, the practical HSV vaccine product should be prepared from a purified vaccine stock having specific components which will be effective against both HSV type 1 and type 2.

It has been found that among the subunit polypeptides present in the HSV envelope, gA and gB, which are polypeptides common to both HSV type 1 and type 2, can exhibit immunological activity sufficient for preventing infection of the both types of HSV, and the gA and gB can be highly isolated and purified on an industrial scale by the method of the present invention.

An object of the present invention is thus to provide a method for preparation of improved HSV subunit vaccines against both of HSV type 1 and type 2 having high safety, high effectiveness and high stability.

DETAILED EXPLANATION

According to the present invention, highly purified glycoproteins gA and gB can be prepared by subjecting a solution containing such as HSV-specific subunit glycoproteins to affinity chromatography using a gel of specific sulfuric acids.

The solution containing such glycoproteins includes a lysate of mammalian cells infected with HSV (including both of type 1 and type 2, unless otherwise specified), a lysate of partially purified HSV particles from the culture cells.

The culture cells infected with HSV can express HSV specific subunit glycoproteins on the cell membrane as well as virus particle, and these culture cells can be used as the starting material in the present invention. Besides, there can also be used recombinant culture cells being capable of producing HSV gA and gB which are obtained by genetic engineering technique.

HSV can propagate in wide range of hosts, and the natural host is human, but HSV can also infect to and can be grown in monkey, rabbit, guinea pig, hamster, mouse, rat and grown hen's egg. etc. Thus, various mammalian cells sensitive to HSV can be used in the present invention. For example, brephic hamster kidney cells (BHK-21), Green monkey kidney cells (Vero), human embryonic lung cells (HEL), human pharyngeal cancer epithelial cells (Hep-2), primary rabbit kidney cells (PRK), chicken embryo fibroblast, or the like are usable in the present invention.

For isolating the desired gA and gB, the starting material may optionally be subjected to pretreatment. For example, the HSV-infected culture cells or the culture supernatant is subjected to the treatment with a homogenizer or ultrasonic treatment to destroy the cells and then the resulting HSV-containing solution is centrifuged to remove crude insoluble materials such as cell pieces to give a dispersion of purified HSV particles. The thus obtained HSV particles dispersion may also be subjected to the affinity chromatography of the present invention.

The starting materials as above-described are subjected to a dissolving treatment with a surfactant. The surfactant used for such dissolving treatment includes anion surfactant such as sodium dodecylsulfate (SDS), sodium deoxycholate, and nonionic and nonionic surfactants such as Triton X-100 (tradename of Polyoxyethylene ether, manufactured by Rohm and Haas Co.), Nonidet P-40 (tradename of octylphenoxypolyethoxyethanol, manufactured by Shell Company), Tween-20 (tradename of polyoxyethylene sorbitan monolaurate, manufactured by Bio-Rad), but preferably nonionic surfactants. The addition amount of the surfactant is usually 0.1 to 10 v/v %, preferably 0.5 to 2.0 v/v %.

The dissolving treatment is usually carried out by adding a required amount of a surfactant to a dispersion of HSV specific subunit glycoproteins and allowing to stand or stirring the mixture at a temperature of 0° to 25° C. for 24 hours.

The glycoproteins extracted by the above dissolving treatment will be re-combined unless any surfactant is present in the system and, according to the present invention the glycoproteins-containing solution is subjected to affinity chromatography with sulfuric acid ester of cellulose or a crosslinked polysaccharide, in the presence of an anionic surfactant or nonionic surfactant, by which the desired gA and gB are isolated.

The sulfuric acid ester of cellulose to be used in the present invention includes a sulfuric acid ester of crystalline cellulose or cellulose having crystalline area and non-crystalline area. These starting celluloses are commercially available, for example, as Abicel (manufactured by Asahi Kasei in Japan), Cellulofine GC-15, GH-25, GC-100, or GC-200 (manufactured by Chisso Corp. in Japan).

The sulfuric acid ester of a crosslinked polysaccharide to be used in the present invention includes a sulfuric acid ester of polysaccharide, such as dextran, cellulose, agarose, which is crosslinked with a crosslinking agent, such as epichlorohydrin, dichlorohydrin, dibromohydrin, ethylene glycol bisepoxypropyl ether. The crosslinked polysaccharides are commercially available, for example, as crosslinked dextran such as Sephadex G-10, G-25, G-50, and G-100 (manufactured by Pharmacia in Sweden), crosslinked agarose such as Sepharose Cl-2B, Cl-4B, and Cl-6B (manufactured by Pharmacia in Sweden), and crosslinked celluloses such as Cellulofine GCL-25, GCL-90 (manufactured by Chisso Corp. in Japan).

The method of the present invention is based on the fact that the gels as described above have an affinity to certain polypeptides from HSV. Thus, such gels have a nature of adsorbing the specific subunits, i.e. gA and gB, which are common to HSV-1 and HSV-2, and does not adsorb any other substances from HSV (e.g. β-lipoprotein). Such gel for chromatography to be used in the present invention is characterized in that it is prepared by directly sulfating agent such as chlorosulfonic acid or anhydrous sulfuric acid in an organic solvent (e.g. pyridine). Thus, the resultant gel is water-insoluble and highly stable. Further, the gel of the sulfuric acid ester of cellulose or a crosslinked polysaccharide exhibits an extremely high adsorbing activity since it is fully sulfated, even at the inner regions thereof. The use of the gel is also advantageous from an economical standpoint, because it can be easily prepared at a low cost. The degree of sulfation (content of the sulfonyl group) of crosslinked polysaccharide is usually in the range of 0.1 to 40 %, preferably 10 to 40 %, based on the weight of the crosslinked polysaccharide, and the degree of sulfation of cellulose is usually in the range of 0.1 to 5.0 %, based on the cellulose.

The method of the invention can be carried out in the following manner. Firstly, a sulfuric ester of cellulose or a polysaccharide is packed within a column, which is equilibrated with a suitable buffer solution having an ionic strength about 0.001–1.0 and a pH of 5–8, containing 0.05–2.0 % of surfactant, which may be selected from the ones used in the above-mentioned dissolving treatment of HSV-containing material preferably 0.1–0.5 %. Such buffer solution may be exemplified by 0.01 M phosphate buffer solution containing 0.1 M NaCl. After the equilibration, a solution containing HSV-specific subunit polypeptides (gA and gB) prepared by the dissolving treatment, and diluted with the same buffer solution as used for the equilibration so that not more than 100 mg per ml of protein is present, is passed through the column in order to adsorb the polypeptides onto the gel, followed by washing sufficiently with the same surfactant-containing buffer solution as used for the equilibration. Thereafter, the adsorbed polypeptides are eluted from the column by passing through the column a suitable buffer solution having an ionic strength larger than that of the surfactant-containing buffer solution used for the equilibration or the washing, for example, 0.01 M phosphate buffer solution containing 0.6 M NaCl and surfactant. The eluate is fractioned, and the fraction containing gA and gB is collected. From this fraction was prepared a starting material for a subsequent gel filtration, by dialysis of the fraction against a buffer solution which will be used for the gel filtration.

A suitable buffer solution for the gel filtration is the same buffer solution as used for above-mentioned affinity chromatography, i.e., a solution having a pH of 5–8 and an ionic strength about 0.001–1.0, containing 0.05–2.0 %, preferably 0.1–0.5 % of surfactant.

A gel material for the gel filtration in the present invention includes a poly-saccharide or crosslinked polyacrylamide such as cellulose, agarose, or crosslinked dextran, which are commercially available, for example, as Sephacryl B, Sephadex, Sepharose (manufactured by Pharmacia in Sweden), Bio-Gel P (manufactured by Bio-Rad) Cellulofine (manufactured by Chisso Corp. in Japan) but is not limited to them as long as they can provide molecular-sieving effects.

By the gel filtration, there are obtained various substances such as those having molecular weights of about 130,000, about 95,000 and about 50,000, among which a fraction having molecular weights of about 90,000 to 100,000 us collected as the desired product. This fraction causes the agglutination reaction with anti-gA and -gB monoclonal antibody-sensitized sheep red blood cell, which fact indicates that the fraction consists of gA and gB. In fact, this fraction, when determined by sodium dodecylsulfate polyacrylamide gel electrophoresis, provides the substantially the same pattern as gA and gB prepared by affinity chromatography in which there is used a ligand of the monoclonal antibody.

After the gel filtration, the fraction was appropriately condensed, dializing with a buffer solution containing 0.01–0.1 %, preferably 0.02–0.05 %, of one of or more nonionic sufactant such as Tween 80, Triton X-100 and so forth.

It is demonstrated that the product thus obtained by the present invention contains no impurities when analyzed by electrophresis with SDS-polyacrylamide gel or by immunoblotting method.

A vaccine is usually prepared by adding an immuno adjuvant (e.g. aluminum gel) in order to enhance the antibody producibility when vaccinated. To the gB-adsorbed aluminum gel suspension thus obtained may be added a preservative (e.g. thimerosal) in an amount of 0.005 to 0.1 w/v % to give the aluminum gel-added vaccine. The gB-adsorbed aluminum gel suspension may be mixed with a stabilizer and optionally a preservative, and then the mixture is lyophilized.

The lyophilized prepartion of HSV subunit vaccine thus obtained can be kept with good storage stability without lowering of antigen titer and further can be dissolved rapidly in an injection solution when used.

The present invention is illustrated by the following Preparations and Example, but should not be construed to be limited thereto.

PREPARATION 1

Preparation of crude solution for chromatography.

Vero cells infected with HSV type 1 KOS strain is collected 24 hours after the infection, and are dissolved by treating with PBS (pH 7.2–7.4) containing 1 v/v % Triton X-100 at 4° C. for one hour. The dissolved solution is centrifuged at 100,000 G for one hour, and then, the supernatant is collected as a crude glycoproteins-containing solution.

PREPARATION 2

To pyridine (200 ml) is added dropwise chlorosulfonic acid (11 ml) at below 0° C. After the addition, the mixture is heated to 65°–70° C. To the mixture is added crosslinked agarose (Sepharose CL-6B, manufactured by Pharmacia) (7.5 g), and the mixture is stirred at 65°–70° C. for 4 hours. After the reaction, the reaction mixture is cooled and then neutralized with aqueous sodium hydroxide. The gel thus obtained is separated by filtration and washed well with 0.01 M phosphate buffered saline solution to give a crosslinked agarose sulfate.

PREPARATION 3

To a mixture (210 ml) of pyridine-chlorosulfonic acid prepared in the same manner as described in the above Preparation 2 is added epichlorohydrin-crosslinked dextran (Sephadex G-50, manufactured by Pharmacia in Sweden)(7.5 g), and the mixture is reacted at 65°–70° C. for 4 hours. After the reaction, the reaction mixture is cooled and neutralized with aqueous sodium hydroxide. The gel thus obtained is separated by filtration and washed well with 0.01 M phosphate buffered saline solution to give a crosslinked cellulose sulfate (7.2 g).

PREPARATION 4

To a mixture (210 ml) of pyridine-chlorosulfonic acid prepared in the same manner as described in the above Preparation 3 is added crosslinked cellulose gel (Cellulofine GLC-25, manufactured by Chisso Corp. in Japan) (30 ml) which has been impregnated with pyridine, and the mixture is reacted at 65°–70° C. for 4 hours. After the reaction, the mixture is cooled and neutralized with aqueous sodium hydroxide. The gel thus obtained is separated by filtration and washed well with 0.01 M phosphate buffered saline solution to give a crosslinked agarose sulfate (23 ml).

EXAMPLE

A sulfate gel (200 ml) obtained in the manner as described in Preparation 2-4 is packed within a column and the packed column is equilibrated with 0.01 M phosphate buffered saline solution (pH 7.2) containing 0.1 % Triton X-100 (600 ml). Then, through the column is passed 100 ml of the supernatant obtained in Preparation 1 (the amount of Protein: about 100 mg/ml), followed by washing with 600 ml of the buffer solution as used for the equilibration. Thereafter, the adsorbed material is eluted from the column by passing through the column 0.01 M phosphate buffer solution containing 0.1 % Triton X-100 and 0.6 M NaCl(pH 7.2). The eluate is fractionated, and the fractions are determined if they contain gA and gB or not by r-PHA method using anti-gA and anti-gB mouse monoclonal antibody sensitized sheep red blood cell, and then the fraction containing gA and gB is pooled. After the pooled solution is dialized with 0.01 M phosphate buffered saline (pH 7.2) containing 0.1 % Triton X-100, the solution is condensed with minicon B-15 (manufactured by Amicon) in order to get a sample (4 ml) for gel filtration.

The Cellulofine GC-700 (manufactured by Chisso Corp in Japan) is packed within a column (15 mmo×1,000 mm) and the column is equilibration with 0.01 M phosphate buffered saline solution (pH 7.2) containing 0.1 % Triton X-100. Then through the column is passed 1 ml of the sample for the gel filtration. The gel filtration is carried out in usual manner. Each fraction is determined whether gA and gB are present or not by r-PHA method using anti-gA and anti-gB mouse monoclonal antibody sheep sensitized red blood cell, and the fraction containing gA and gB is pooled.

The fraction gives the same electropholitic pattern as the pure gA and gB vaccine solution obtained with the monoclonal antibody, when analyzed by sodium dodesylsulfate polyacrylamide electropharesis and the molecular weight of the proteins in the fraction is about 95,000. After the dialysis of the pooled fraction with 0.01 M phosphate buffered saline containing 0.05 % Triton X-100, there is obtained herpes simplex virus subunit vaccine stock solution.

The stock solution was added with 0.01 M phosphate buffered saline solution containing 0.05 % Triton X-100, wherein the amount of protein is adjusted to a content ration of 50 µg/ml, and after sterilizing the filtration, the solution is divided and poured into vials (each content: 1 ml).

What is claimed is:

1. A method for the preparation of a herpes simplex virus subunit vaccine, which comprises subjecting a solution containing glycoproteins gA and gB to column chromatography, using as a gel for chromatography, a sulfuric acid ester of cellulose or a crosslinked polysaccharide to adsorb the glycoproteins gA and gB onto the gel in the presence of an anionic surfactant or nonionic surfactant, said sulfuric acid ester being prepared by treating a gel of cellulose or crosslinked polysaccharide with a sulfating agent in an organic solvent, eluting the adsorbed glycoproteins to obtain an eluate containing the glycoproteins, and subjecting the eluate to gel filtration to obtain a filtrate containing the glycoproteins.

2. The method as claimed in claim 1, wherein the glycoproteins-containing solution is obtained from culture cells infected with herpes simplex virus subunit vaccine.

3. The method as claimed in claim 1, wherein the sulfuric acid ester of crosslinked polysaccharide is selected from the group consisting of a crosslinked cellulose sulfate, a crosslinked agarose sulfate and a crosslinked dextran sulfate.

4. The method as claimed in claim 1, wherein the sulfuric acid ester of cellulose is a sulfuric acid ester of crystalline cellulose or a cellulose having a crystalline area and non-crystalline area.

* * * * *